US009757576B2

(12) United States Patent
Sullivan et al.

(10) Patent No.: US 9,757,576 B2
(45) Date of Patent: Sep. 12, 2017

(54) RELIABLE READINESS INDICATION FOR A WEARABLE DEFIBRILLATOR

(71) Applicant: West Affum Holdings Corp., Grand Cayman (KY)

(72) Inventors: Joseph Leo Sullivan, Kirkland, WA (US); Isabelle Banville, Newcastle, WA (US); Blaine Krusor, Seattle, WA (US); Daniel Ralph Piha, Bellevue, WA (US); Laura Marie Gustavson, Redmond, WA (US); David Peter Finch, Bothell, WA (US); Kenneth Frederick Cowan, Kirkland, WA (US); Richard C Nova, Seattle, WA (US)

(73) Assignee: WEST AFFUM HOLDINGS CORP., Grand Cayman (KY)

( * ) Notice: Subject to any disclaimer, the term of this patent is extended or adjusted under 35 U.S.C. 154(b) by 0 days.

(21) Appl. No.: 14/662,102

(22) Filed: Mar. 18, 2015

(65) Prior Publication Data

US 2015/0321022 A1   Nov. 12, 2015

Related U.S. Application Data

(60) Provisional application No. 61/955,005, filed on Mar. 18, 2014, provisional application No. 61/954,836, filed on Mar. 18, 2014.

(51) Int. Cl.
*A61N 1/39* (2006.01)
*A61N 1/04* (2006.01)

(52) U.S. Cl.
CPC .............. *A61N 1/39* (2013.01); *A61N 1/046* (2013.01); *A61N 1/0484* (2013.01); *A61N 1/3925* (2013.01); *A61N 1/3968* (2013.01); *A61N 1/3993* (2013.01)

(58) Field of Classification Search
CPC ....... A61N 1/0484; A61N 1/39; A61N 1/3925
See application file for complete search history.

(56) References Cited

U.S. PATENT DOCUMENTS

| 3,724,455 A | 4/1973 | Unger |
|---|---|---|
| 4,583,524 A | 4/1986 | Hutchins |
| 4,619,265 A | 10/1986 | Morgan et al. |

(Continued)

FOREIGN PATENT DOCUMENTS

WO   2009/034506   3/2009

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.

(Continued)

*Primary Examiner* — George Evanisko
(74) *Attorney, Agent, or Firm* — Kavounas Patent Law Office, PLLC (57) ABSTRACT

A portable medical device having a reliable readiness indicator. Embodiments provide a reliable readiness indicator with an active clasp that holds the garment in place. The clasp is enabled by the defibrillator when it is ready for use. If the clasp is not enabled the garment cannot be worn comfortably, and it becomes apparent to the patient that steps need to be taken to make the device ready for use.

16 Claims, 11 Drawing Sheets

(56) References Cited

U.S. PATENT DOCUMENTS

| | | | |
|---|---|---|---|
| 4,928,690 A | 5/1990 | Heilman et al. | |
| 4,955,381 A | 9/1990 | Way et al. | |
| 5,078,134 A | 1/1992 | Heilman et al. | |
| 5,228,449 A | 7/1993 | Christ et al. | |
| 5,348,008 A * | 9/1994 | Bornn | A61B 5/0006 |
| | | | 128/903 |
| 5,353,793 A | 10/1994 | Bornn | |
| RE34,800 E | 11/1994 | Hutchins | |
| 5,394,892 A | 3/1995 | Kenny | |
| 5,405,362 A | 4/1995 | Kramer et al. | |
| 5,474,574 A | 12/1995 | Payne et al. | |
| 5,662,690 A | 9/1997 | Cole et al. | |
| 5,782,878 A | 7/1998 | Morgan et al. | |
| 5,792,204 A | 8/1998 | Snell | |
| 5,902,249 A | 5/1999 | Lyster | |
| 5,913,685 A | 6/1999 | Hutchins | |
| 5,919,212 A | 7/1999 | Olson et al. | |
| 6,016,059 A | 1/2000 | Morgan | |
| 6,047,203 A | 4/2000 | Sackner et al. | |
| 6,065,154 A | 5/2000 | Hulings et al. | |
| 6,108,197 A | 8/2000 | Janik | |
| 6,148,233 A * | 11/2000 | Owen | A61N 1/0452 |
| | | | 607/5 |
| 6,201,992 B1 | 3/2001 | Freeman | |
| 6,263,238 B1 | 7/2001 | Brewer et al. | |
| 6,287,328 B1 | 9/2001 | Snyder et al. | |
| 6,304,780 B1 | 10/2001 | Owen et al. | |
| 6,319,011 B1 | 11/2001 | Motti et al. | |
| 6,334,070 B1 | 12/2001 | Nova et al. | |
| 6,356,785 B1 | 3/2002 | Snyder | |
| 6,427,083 B1 | 7/2002 | Owen et al. | |
| 6,529,875 B1 | 3/2003 | Nakajima et al. | |
| 6,546,285 B1 | 4/2003 | Owen et al. | |
| 6,681,003 B2 | 1/2004 | Linder et al. | |
| 6,762,917 B1 | 7/2004 | Verbiest et al. | |
| 7,065,401 B2 | 6/2006 | Worden | |
| 7,559,902 B2 | 7/2009 | Ting et al. | |
| 7,865,238 B2 | 1/2011 | Brink | |
| 7,870,761 B2 | 1/2011 | Valentine et al. | |
| 7,974,689 B2 | 7/2011 | Volpe et al. | |
| 8,140,154 B2 | 3/2012 | Donnelly et al. | |
| 8,224,441 B2 | 7/2012 | Vaisnys et al. | |
| 8,369,944 B2 | 2/2013 | Macho et al. | |
| 8,644,925 B2 | 2/2014 | Volpe et al. | |
| 8,965,500 B2 | 2/2015 | Macho et al. | |
| 9,008,801 B2 | 4/2015 | Kaib et al. | |
| 9,131,901 B2 | 9/2015 | Volpe et al. | |
| 9,132,267 B2 | 9/2015 | Kaib | |
| 2003/0158593 A1 | 8/2003 | Heilman et al. | |
| 2005/0107833 A1 | 5/2005 | Freeman et al. | |
| 2005/0107834 A1 | 5/2005 | Freeman et al. | |
| 2008/0312709 A1 | 12/2008 | Volpe et al. | |
| 2009/0005827 A1 | 1/2009 | Weintraub et al. | |
| 2010/0007413 A1 | 1/2010 | Herleikson | |
| 2010/0298899 A1 | 11/2010 | Donnelly et al. | |
| 2011/0022105 A9 | 1/2011 | Owen et al. | |
| 2011/0288604 A1 | 11/2011 | Kaib et al. | |
| 2011/0288605 A1 | 11/2011 | Kaib et al. | |
| 2012/0112903 A1 | 5/2012 | Kaib et al. | |
| 2012/0144551 A1 | 6/2012 | Guldalian | |
| 2012/0150008 A1 | 6/2012 | Kaib et al. | |
| 2012/0158075 A1 | 6/2012 | Kaib et al. | |
| 2012/0265265 A1 | 10/2012 | Razavi et al. | |
| 2012/0283794 A1 | 11/2012 | Kaib et al. | |
| 2012/0302860 A1 | 11/2012 | Volpe et al. | |
| 2013/0085538 A1 | 4/2013 | Volpe et al. | |
| 2013/0231711 A1 | 9/2013 | Kaib | |
| 2013/0245388 A1 | 9/2013 | Rafferty et al. | |
| 2013/0274565 A1 | 10/2013 | Langer et al. | |
| 2013/0317852 A1 | 11/2013 | Worrell et al. | |
| 2013/0325078 A1 | 12/2013 | Whiting et al. | |
| 2014/0025131 A1 | 1/2014 | Sullivan et al. | |
| 2014/0070957 A1 | 3/2014 | Longinotti-Buitoni et al. | |
| 2014/0324112 A1 | 10/2014 | Macho et al. | |
| 2014/0378812 A1 | 12/2014 | Saroka et al. | |
| 2015/0039053 A1 | 2/2015 | Kaib et al. | |
| 2016/0004831 A1 | 1/2016 | Carlson et al. | |

OTHER PUBLICATIONS

LIFECOR LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Heartstart MRx and XL AED Algorithm—Application Note, Jul. 2001, Edition 2 Philips Healthcare, USA.

The LifeVest Network/Patient Data Management System, Zoll, 2015, 20C0503 Rev A.

* cited by examiner

FIG. 1 *DEFIBRILLATION SCENE*

| TYPE OF EXTERNAL DEFIBRILLATOR | INTENDED TO BE USED BY PERSONS: | |
| --- | --- | --- |
| | IN THE MEDICAL PROFESSIONS | NOT IN THE MEDICAL PROFESSIONS |
| DEFIBRILLATOR – MONITOR | √ | |
| AED | √ | √ |

FIG. 2 *TWO MAIN TYPES OF EXTERNAL DEFIBRILLATORS*

FIG. 3

COMPONENTS OF EXTERNAL DEFIBRILLATOR

RELIABLE READINESS INDICATION FOR A WEARABLE DEFIBRILLATOR

CROSS REFERENCE TO RELATED APPLICATIONS

This patent application claims the benefit of and priority to U.S. Provisional Patent Application Ser. No. 61/955,005, filed on Mar. 18, 2014, entitled "Foolproof Readiness Indication For A Wearable Defibrillator," and U.S. Provisional Patent Application Ser. No. 61/954,836, filed on Mar. 18, 2014, entitled "Hybrid Electrode To Monitor ECG And Detect Electrode Motion Relative To Skin Surface" the disclosures of which are hereby incorporated by reference for all purposes.

TECHNICAL FIELD

The disclosed subject matter pertains generally to the area of medical devices, and more specifically to the area of wearable cardioverter defibrillators.

BACKGROUND INFORMATION

Sudden Cardiac Arrest (SCA) is a sudden stop in effective blood circulation due to the failure of the heart to contract effectively or at all. Timely defibrillation is the single most important factor in saving an SCA victim's life. A treatment shock should be delivered within a few minutes after an event to be effective. Some studies show that an SCA victim's chance of survival drops 10 percent with each passing minute.

A Wearable Cardioverter Defibrillator (WCD or "wearable defibrillator") may be worn by patients at risk of SCA. The WCD is generally lightweight and easy to wear, allowing patients to return to their activities of daily living, while having the peace of mind that they are protected from SCA. The WCD generally contains two main components—a garment and a monitor. The garment, worn under the clothing, detects arrhythmias and delivers treatment shocks. The monitor is generally worn around the waist or from a shoulder strap and records arrhythmias. The WCD continuously monitors the patient's heart and, if a life-threatening heart rhythm is detected, the device delivers a treatment shock to restore normal heart rhythm.

A WCD might be unready for use for a variety of reasons—the battery could be low, the battery could be disconnected, the electrodes could be disconnected or not ready for use, there could be a failure of a device self-test, etc. Accordingly, it is important that when a patient puts on a WCD that the device is ready for use. Existing WCDs use simple indicators to inform the patient of device readiness, but these can be obscure, confusing, and easy to ignore. An improved mechanism for reducing the likelihood that a WCD will be donned without being in a ready state has eluded those skilled in the art, until now.

SUMMARY OF EMBODIMENTS

Embodiments are directed to a reliable readiness indicator for a wearable defibrillator. One specific embodiment provides a reliable readiness indicator with an active clasp that holds the garment in place. The clasp is enabled by the defibrillator when it is ready for use. If the clasp is not enabled the garment cannot be worn, and it becomes apparent to the patient that steps need to be taken to make the device ready for use. An alternative embodiment implements a retractable protrusion that makes the wearable defibrillator uncomfortable unless the defibrillator is in an operative condition. Another alternative embodiment implements electroluminescent components that illuminate to indicate the defibrillator is in the operative condition. Still another embodiment implements audible cues that announce a warning if the defibrillator is inoperative. Yet another embodiment implements a wireless transmission component configured to transmit an alert if the defibrillator is inoperative.

BRIEF DESCRIPTION OF THE DRAWINGS

FIG. 2 is a table listing two main types of the external defibrillator shown in FIG. 1, and who they might be used by.

DETAILED DESCRIPTION

Generally described, the disclosure is directed to a reliable readiness indicator for a wearable defibrillator. Embodiments of the readiness indicator may be incorporated into one of the steps that a person must perform when putting the garment on. If the defibrillator is not ready, then the garment cannot be put on.

Description of Operative Environment for Embodiments

Figure 1:
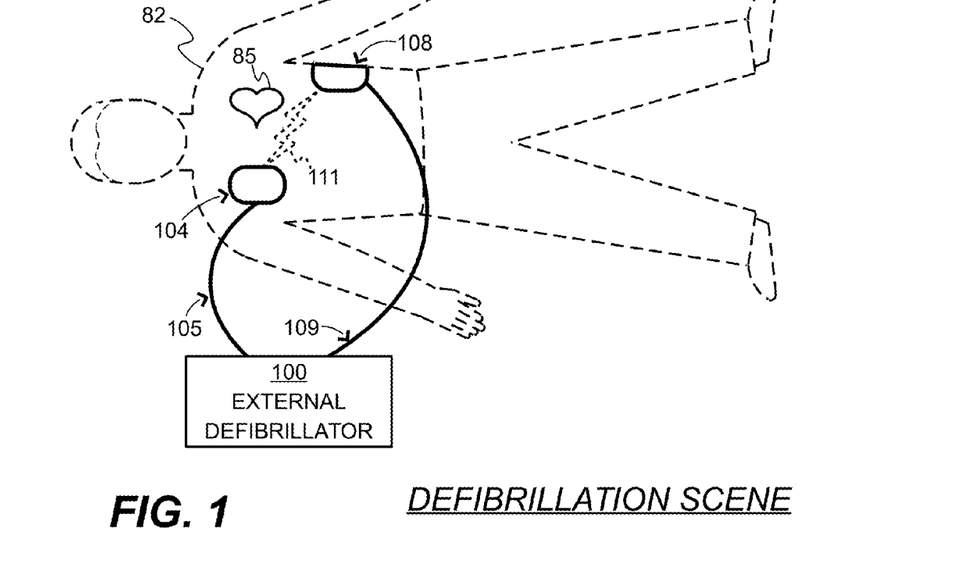
FIG. 1 is a diagram of a scene where an external defibrillator is used to try and save the life of a person in accordance with an embodiment.

FIG. 1 is a diagram of a defibrillation scene. A person 82 is lying supine. Person 82 could be a patient in a hospital or someone found unconscious. Person 82 is experiencing a condition in their heart 85, which could be, by way of an example, Ventricular Fibrillation (VF).

A portable external defibrillator 100 has been brought close to person 82. The portable external defibrillator can also be a wearable or hybrid defibrillator 82. At least two defibrillation electrodes 104, 108 are usually provided with external defibrillator 100. Electrodes 104, 108 are coupled with external defibrillator 100 via respective electrode leads 105, 109. A rescuer (not shown) has attached electrodes 104, 108 to the skin of person 82. Defibrillator 100 is administering, via electrodes 104, 108, a brief, strong electric pulse 111 through the body of person 82. Pulse 111, also known as a defibrillation shock, goes also through heart 85, in an attempt to restart it, for saving the life of person 82.

Defibrillator 100 can be one of different types, each with different sets of features and capabilities. The set of capabilities of defibrillator 100 is determined by planning who would use it, and what training they would be likely to have. Examples are now described.

Figure 2:
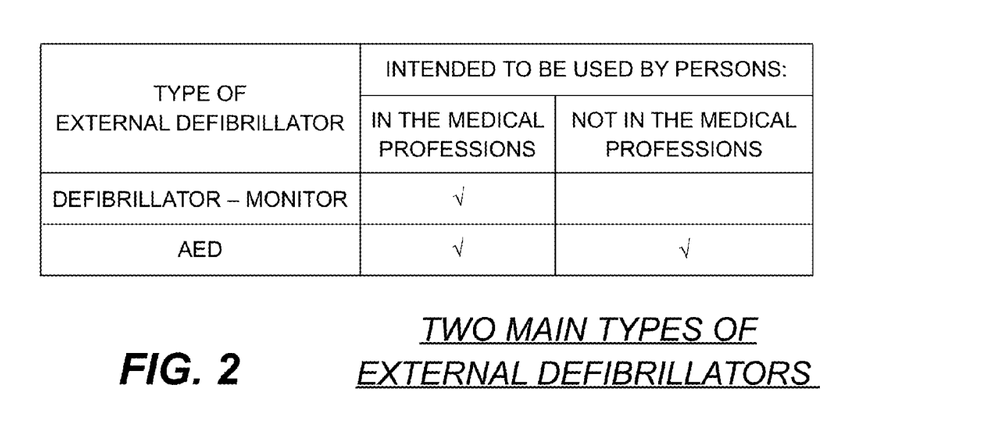

FIG. 2 is a table listing examples of types of external defibrillators and their primary intended users. A first type of defibrillator 100 is generally called a defibrillator-monitor (or monitor-defibrillator) because it is typically formed as a single unit in combination with a patient monitor. A defibrillator-monitor is intended to be used by medical professionals, such as doctors, nurses, paramedics, emergency medical technicians, etc. Such a defibrillator-monitor is generally intended to be used in a pre-hospital or hospital scenario.

As a defibrillator, the device can be one of different varieties, or even versatile enough to be able to switch among different modes that individually correspond to the varieties. One variety is that of an automated defibrillator, which can determine whether a shock is needed and, if so, charge to a predetermined energy level and instruct the user to administer the shock. Another variety is that of a manual defibrillator, where the user determines the need and controls administering the shock.

As a patient monitor, the device has features additional to what is minimally needed for mere operation as a defibrillator. These features can be for monitoring physiological indicators of a person in an emergency scenario. These physiological indicators are typically monitored as signals, such as a person's full ECG (electrocardiogram) signals, or impedance between two electrodes. Additionally, these signals can be about the person's temperature, non-invasive blood pressure (NIBP), arterial oxygen saturation/pulse oximetry (SpO2), the concentration or partial pressure of carbon dioxide in the respiratory gases, which is also known as capnography, and so on. These signals can be further stored and/or transmitted as patient data.

A second type of external defibrillator 100 is generally called an AED, which stands for "Automated External Defibrillator." An AED typically makes the shock/no shock determination by itself, automatically. It can typically sense enough physiological conditions of the person 82 using only the defibrillation electrodes 104, 108 shown in FIG. 1. An AED can either administer the shock automatically, or instruct the user to do so, e.g. by pushing a button. Being of a much simpler construction, an AED typically costs much less than a defibrillator-monitor. As such, it makes sense for a hospital, for example, to deploy several AEDs throughout, in case the more expensive defibrillator-monitor is engaged at an Intensive Care Unit, or the like.

AEDs, however, can also be used by people who are not in the medical profession. More particularly, an AED can be used by many professional first responders, such as policemen, firemen, etc. Even a person with only first-aid training can use one. And AEDs increasingly can supply instructions to whoever is using them.

AEDs are thus particularly useful when a person suffers from VF because it is so critical to respond quickly. However, the people who will first reach the VF sufferer may not be medical professionals. Increasing awareness has resulted in AEDs being deployed in public or semi-public spaces, so that even a member of the public can use one if they have obtained first aid and CPR/AED training on their own initiative. This way, defibrillation can be administered soon enough after the onset of VF, to hopefully be effective in rescuing the person.

There are other types of external defibrillators in addition to those listed in FIG. 2. For example, a hybrid defibrillator can have aspects of an AED and also of a defibrillator-monitor. A usual such aspect is additional ECG monitoring capability.

Figure 3:
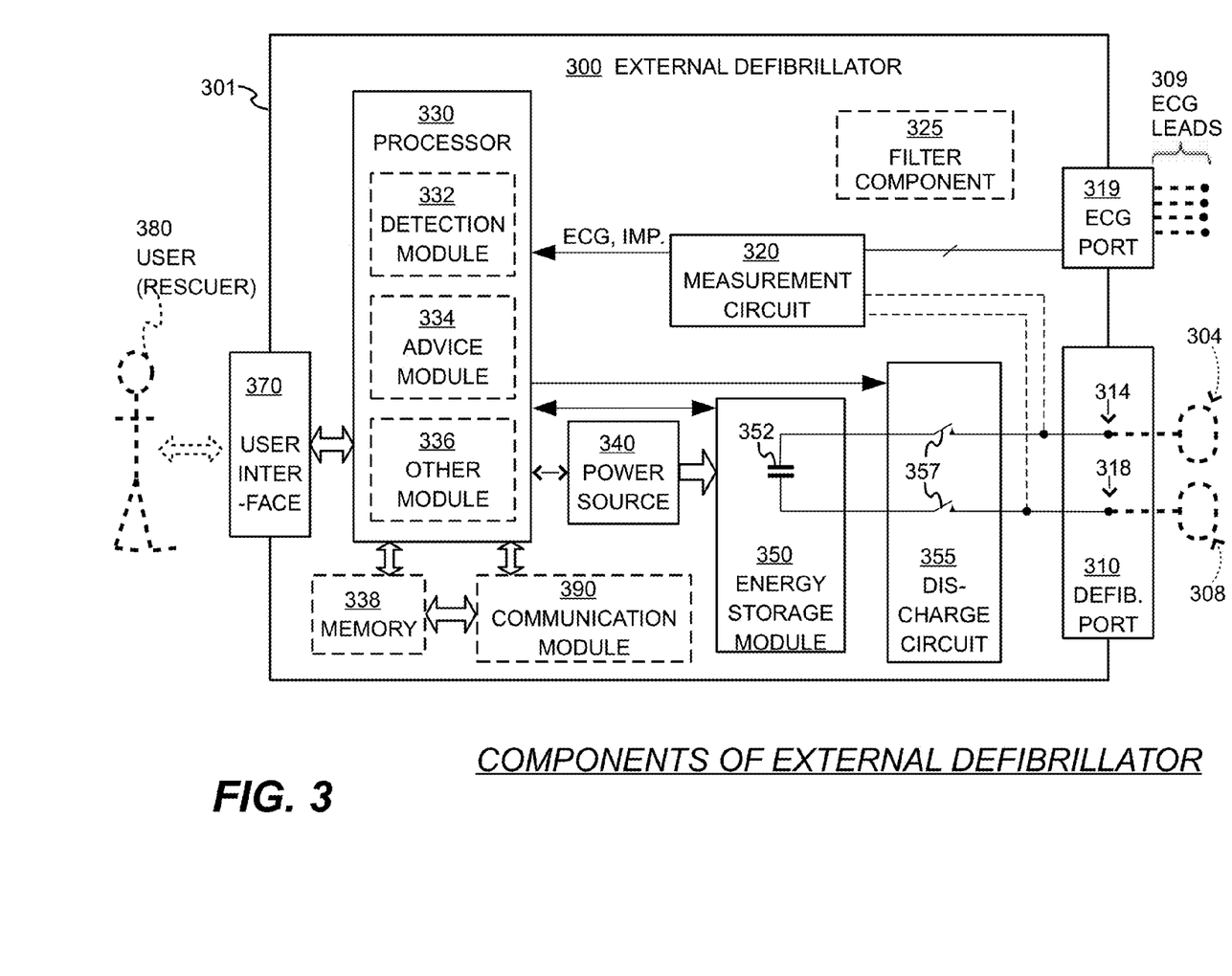
FIG. 3 is a diagram showing components of an external defibrillator 300 made according to embodiments

FIG. 3 is a diagram showing components of an external defibrillator 300 made according to embodiments. These components can be, for example, in external defibrillator 100 of FIG. 1. Plus, the components shown in FIG. 3 can be provided in a housing 301, also known as a casing.

External defibrillator 300 is intended for use by a user 380, who would be the rescuer. Defibrillator 300 typically includes a defibrillation port 310, such as a socket in housing 301. Defibrillation port 310 includes nodes 314, 318. Defibrillation electrodes 304, 308, which can be similar to electrodes 104, 108, can be plugged in defibrillation port 310, so as to make electrical contact with nodes 314, 318, respectively. It is also possible that electrodes can be connected continuously to defibrillation port 310, etc. Either way, defibrillation port 310 can be used for guiding via electrodes to person 82 an electrical charge that has been stored in defibrillator 300, as discussed below.

If defibrillator 300 is a defibrillator-monitor, as was described with reference to FIG. 2, it will typically also have an ECG port 319 in housing 301, for plugging in ECG leads 309. ECG leads 309 can help sense an ECG signal, such as a common 12-lead signal. Other types of ECG signal leads are equally applicable. A defibrillator-monitor could have additional ports that are not shown.

The defibrillator 300 may optionally include a filter component 325 structured to filter the ECG signal. In one specific implementation, the filter component 325 may be a comb filter used to remove chest compression artifacts from the ECG signal. Chest compression artifacts are a type of noise introduced into the ECG signal as a result of chest compressions being delivered to the person 82.

Defibrillator 300 also includes a measurement circuit 320. Measurement circuit 320 receives physiological signals from ECG port 319, and also from other ports, if provided. These physiological signals are sensed, and information about them is rendered by measurement circuit 320 as data, or other signals, etc.

If defibrillator 300 is an AED, it may lack ECG port 319. In that case, measurement circuit 320 could obtain physiological signals through nodes 314, 318 instead, when defibrillation electrodes 304, 308 are attached to person 82. In these cases, a person's ECG signal can be sensed as a voltage difference between electrodes 304, 308. Plus, impedance between electrodes 304, 308 can be sensed for detecting, among other things, whether these electrodes 304, 308 have been inadvertently disconnected from the person.

Defibrillator 300 also includes a processor 330, which may be implemented in any number of ways. Such ways include, by way of example and not of limitation, digital and/or analog processors such as microprocessors and digital-signal processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 330 can be considered to have a number of modules. One such module can be a detection module 332, which senses outputs of measurement circuit 320. Detection module 332 can include a VF detector. Thus, the person's sensed ECG can be used to determine whether the person is experiencing VF.

Another such module in processor 330 can be an advice module 334, which arrives at advice based on outputs of detection module 332. Advice module 334 can include a Shock Advisory Algorithm, implement decision rules, and so on. The advice can be to shock, to not shock, to administer other forms of therapy, and so on. If the advice is to shock, some external defibrillator embodiments merely report that to the user, and prompt them to do it. Other embodiments further execute the advice, by administering the shock. If the advice is to administer CPR, defibrillator 300 may further issue prompts for it, and so on.

Processor 330 can include additional modules, such as module 336, for other functions to numerous to list here. In addition, if other component 325 is indeed provided, it may be operated in part by processor 330, etc.

Defibrillator 300 optionally further includes a memory 338, which can work together with processor 330. Memory 338 may be implemented in any number of ways. Such ways include, by way of example and not of limitation, nonvolatile memories (NVM), read-only memories (ROM), random access memories (RAM), any combination of these, and so on. Memory 338, if provided, can include programs for processor 330, and so on. In addition, memory 338 can store prompts for user 380, etc. Moreover, memory 338 can store patient data.

Defibrillator 300 may also include a power source 340. To enable portability of defibrillator 300, power source 340 typically includes a battery. Such a battery is typically implemented as a battery pack, which can be rechargeable or not. Sometimes, a combination is used, of rechargeable and non-rechargeable battery packs. Other embodiments of power source 340 can include AC power override, for where AC power will be available, and so on. In some embodiments, power source 340 is controlled by processor 330.

Defibrillator 300 additionally includes an energy storage module 350. Module 350 is where some electrical energy is stored, when preparing it for sudden discharge to administer a shock. Module 350 can be charged from power source 340 to the right amount of energy, as controlled by processor 330. In typical implementations, module 350 includes one or more capacitors 352, or the like.

Defibrillator 300 moreover includes a discharge circuit 355. Discharge circuit 355 can be controlled to permit the energy stored in module 350 to be discharged to nodes 314, 318, and thus also to defibrillation electrodes 304, 308. Discharge circuit 355 can include one or more switches 357. Those can be made in a number of ways, such as by an H-bridge, or the like.

Defibrillator 300 further includes a user interface 370 for user 380. User interface 370 can be made in any number of ways. For example, interface 370 may include a screen, to display what is detected and measured, provide visual feedback to the rescuer for their resuscitation attempts, and so on. Interface 370 may also include a speaker to issue audible signals, such as voice prompts, or the like. The user interface 370 may issue prompts to the user 380, visually or audibly, so that the user 380 can administer CPR, for example. Interface 370 may additionally include various controls, such as pushbuttons, keyboards, and so on. In addition, discharge circuit 355 can be controlled by processor 330, or directly by user 380 via user interface 370, and so on.

Defibrillator 300 can optionally include other components. For example, a communication module 390 may be provided for communicating with other machines. Such communication can be performed wirelessly, or via wire, or by infrared communication, and so on. This way, data can be communicated, such as patient data, incident information, therapy attempted, CPR performance, and so on.

Embodiments of a Wearable Defibrillator with an Active Clasp

Figure 4:
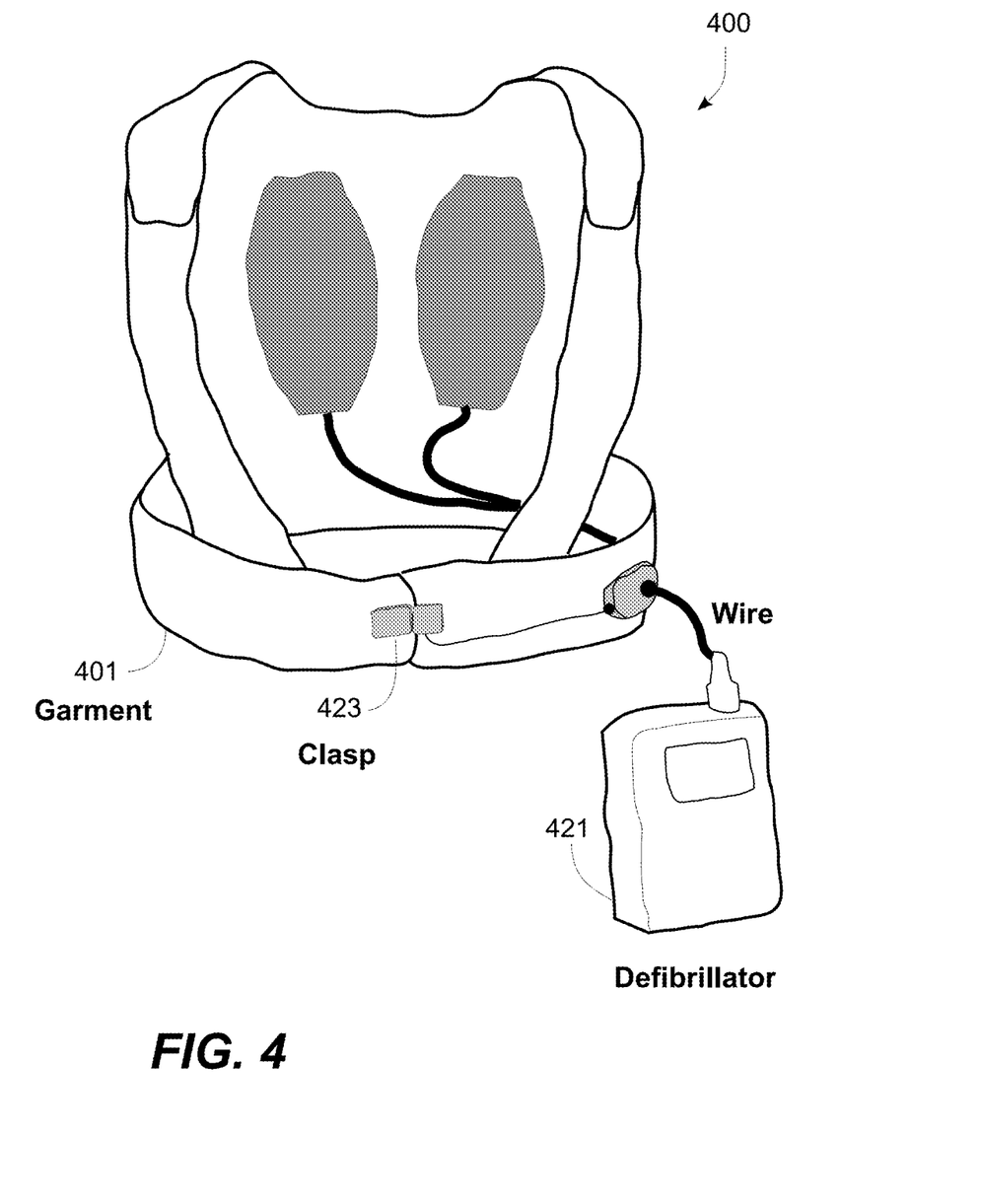
FIG. 4 is a conceptual diagram generally illustrating one embodiment for a reliable readiness indicator for use on a WCD.

FIG. 4 is a conceptual diagram generally illustrating one embodiment for a reliable readiness indicator for use on a WCD. Illustrated is a WCD having a garment 401 and a defibrillator 421. The garment 401 is worn by a patient, and may be prescribed for a patient at high risk of SCA. The defibrillator 421 includes electrodes (not shown) that are attached to the patient during use. In this embodiment, the defibrillator 421 is attached to the garment 401 using a wire connected to a clasp 423. Alternatively, the defibrillator 421 could be wirelessly connected to the clasp 423, such as using Bluetooth, or the like.

Figure 5:
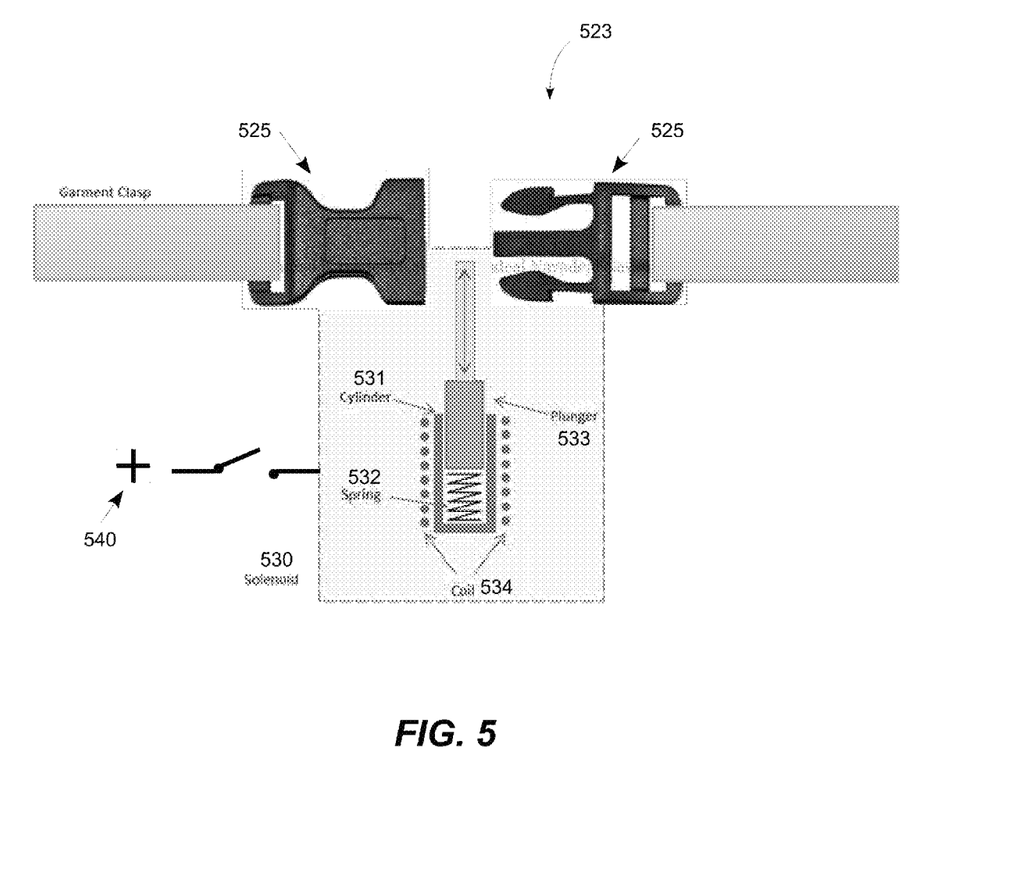
FIG. 5 is a conceptual illustration of a preferred active clasp that may be used in various embodiments.
Figure 6:
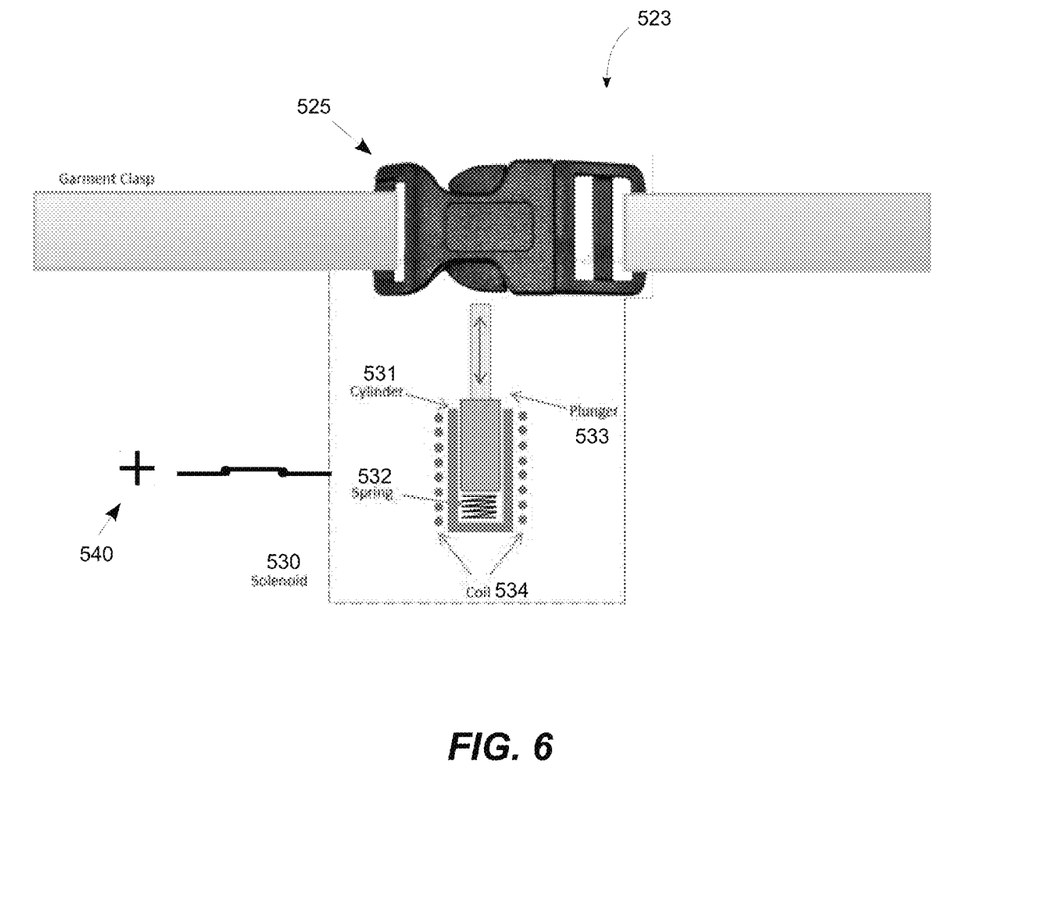
FIG. 6 is another conceptual illustration demonstrating that the active clasp may be engaged if the defibrillator is in operable condition.

In the preferred embodiment, the clasp 423 is an active clasp that is used to close the garment. Preferably, the patient would either need to close the clasp 423 in order to wear the garment 401, or at least be favorably inclined to do so. One specific implementation of the clasp 423 is illustrated in FIGS. 5-6, and described below. Generally stated, the clasp 423 may make use of an active component that prevents the clasp 423 from fully engaging ("clasping") unless the defibrillator 421 portion of the WCD is in operative condition.

In operation, as a patient attempts to put on the garment 401 portion of the WCD, the patient is ideally either required or favorably disposed to engage the clasp 423. As the patient attempts to engage the clasp 423, it will either engage or not. Preferably, whether the clasp 423 engages or not is dependent upon whether the defibrillator 421 portion of the WCD 400 is in operative condition. Accordingly, if the patient learns that the clasp 423 refuses to engage, that will inform the patient to verify whether the defibrillator 421 is in operative condition, thereby avoiding a dangerous situation where the patient is wearing an inoperative WCD.

It may be that the WCD 400 has other clasps in addition to the active clasp 423. In that embodiment, any one or more of the multiple clasps could be an active clasp, like clasp 423. Multiple clasps would allow the patient to put the garment on most of the way even without the active clasp enabled. This feature could allow the defibrillator to verify electrode contact with the skin of the patient even though the active clasp 423 is disabled. However, the garment would be awkward to wear with the clasp 423 undone, so it should be obvious to the patient that steps need to be taken to correct the situation.

FIG. 5 is a conceptual illustration of a preferred active clasp 523 that may be used in various embodiments. Preferably, the active clasp 523 includes a clasp portion 525 and an active component (solenoid 530). In this embodiment, the active component is an electrical solenoid 530 that is in an extended state at rest. The electrical solenoid includes a plunger 533 disposed within a cylinder 531. The cylinder 531 is closed at the opposite end of the plunger 533. A spring 532 is positioned between the plunger 533 and the closed end of the cylinder 531 such that spring tension pushes the plunger 533 partially out of the cylinder 531 in the absence of some external force. An electrical coil 534 encircling the cylinder 531 provides that external force but only when an electrical voltage 540 is applied to the coil 534. However, with no voltage applied to the solenoid, the spring 532 pushes the plunger 533 partially out of the cylinder 531. As illustrated in FIG. 5, the plunger 533 interferes with the path of the clasp portion 525, thereby eliminating the possibility of closing the active clasp 523.

In the preferred embodiment, the voltage 540 is provided by the defibrillator (not shown) when the defibrillator is in operative condition. In one embodiment, the defibrillator may be configured with a self-test function and an output that is only active when the defibrillator passes the self-test function. The self-test function may evaluate any one or more functions of the defibrillator for proper operation, such as whether the batteries are good, all the internal functions are operational, monitoring and therapy pads are attached and operational, or the like. Alternatively, the voltage 540 may be a simple signal that is coupled to a battery on the defibrillator and whenever the defibrillator battery is sufficiently charged, the signal is present. Other alternatives are also possible.

Turning now to FIG. 6, if the defibrillator (not shown) is in operable condition, voltage 540 is coupled to the solenoid 530. As mentioned above, "operable condition" for the defibrillator could be any condition in which designers believe that the WCD is safe to be worn. Operable condition could be as simple as having a charged battery, or it could also (or alternatively) mean that the defibrillator has performed and verified self-tests or other tests, such as electrode attachment, and the like.

In this embodiment, as voltage 540 is applied to the solenoid coil 534, the electrical current flow through the coil 534 creates a magnetic field within the cylinder 531 that retracts the plunger 533 into the cylinder 531, compressing the spring 532. With the plunger 533 retracted, the clasp system 525 can properly be closed to secure the garment on the patient.

In this particular embodiment, a disengagement feature may be added as a warning to the patient. More specifically, when the voltage 540 is removed from the solenoid coil 534, the spring 532 pushes the plunger 533 out of the cylinder 531, thereby disengaging the clasp system. In this way, feedback is provided to the patient that the wearable defibrillator has ceased properly functioning. The plunger 533 may continue to prevent properly closing the clasp system 525 until voltage 540 is returned to the solenoid coil 534. Once voltage 540 is returned to the solenoid coil 534, the plunger 533 retracts again, informing the patient that the wearable defibrillator is properly functioning and ready for use again.

Although an active clasp using an electrical solenoid have been described, it will be appreciated that there may be many other methods of making a reliable readiness indicator for a wearable defibrillator. For example, an armhole of the garment 401 (FIG. 4) could be affixed with an active component that closes unless it is actively enabled by the defibrillator. In another alternative, a connector between the electrodes and the defibrillator might be used and only allow a connection when the defibrillator is ready. These are only examples of the many types of active clasps that may be used for indicating that a wearable defibrillator is unavailable for safe use.

Alternative Reliable Readiness Indicators

Figure 7:
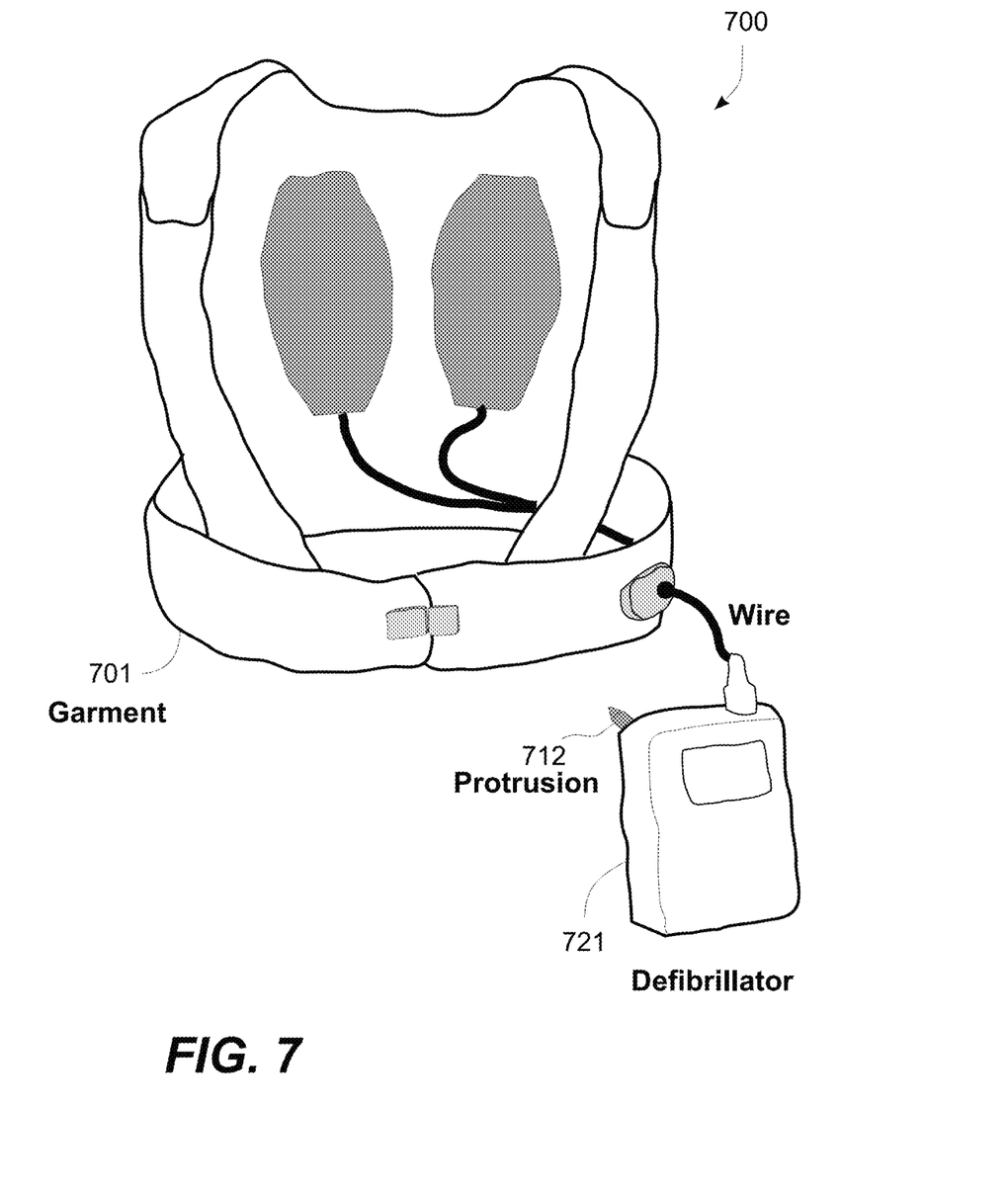
FIG. 7 illustrates yet another embodiment of a reliable readiness indicator for a wearable defibrillator.

FIG. 7 illustrates yet another embodiment of a reliable readiness indicator for a wearable defibrillator. In this embodiment, a WCD includes a garment 701 using a protrusion 712 that pokes the patient if the defibrillator 721 is not ready for use. Similar to the active clasp, the protrusion 712 might be activated by a solenoid, for example, that would cause the protrusion 712 to retract when the defibrillator 721 is ready and extend when the defibrillator 721 is not ready. The protrusion 712 could be integrated into the garment 701 or into the defibrillator 721 itself, making the defibrillator 721 so awkward to wear that it would be obvious to the patient that something needs to be done. In addition, putting the protrusion 712 on the defibrillator 721 (rather than the garment 701) enables the patient to completely don the garment and connect the defibrillator 721 so that it can perform any tests for operability, such as determining whether the electrodes are attached. If the defibrillator 721 passes its self tests (including electrodes) it would retract the protrusion 712. Having the protrusion on the defibrillator 721, rather than the garment 701, avoids the unnecessary discomfort to the patient that would result while the defibrillator 721 was performing its self-tests.

Figure 8:
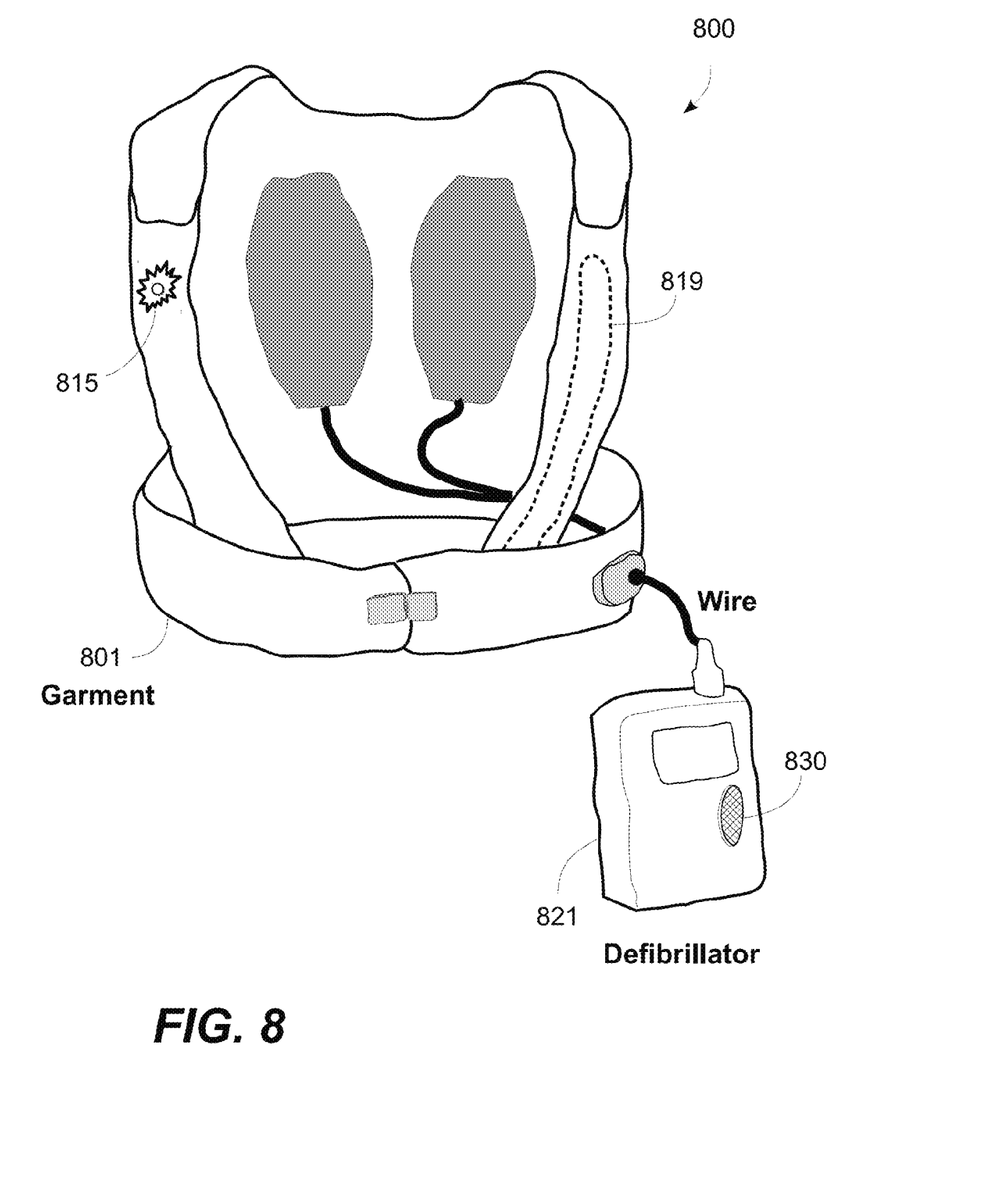
FIG. 8 illustrates yet another embodiment of a reliable readiness indicator that may be implemented as a color indicator in or on the garment when the device is ready.

FIG. 8 illustrates yet another embodiment of a reliable readiness indicator that may be implemented as a color indicator in or on the garment when the device is ready. In this embodiment, a garment 801 includes a color-changing component that is illuminated when the defibrillator 821 is in an operative condition. The color-changing component could be one or more LEDs 815 embedded in the garment and that is illuminated by a signal provided when the defibrillator 821 is in operable condition. Alternatively, the color-changing component could be electroluminescent fibers 819 woven into the garment 801. In addition to or instead of changing the color of the garment, the color of the color-changing component could change when the device is ready. For example, without power, the device may be a natural color, i.e., not illuminated; powered up and ready, the translucent device case may be illuminated by a colored LED. Another alternative may be to use a display with confirmation text or pictogram that uses a memory-LCD, such that the device-status image/text is available even without power. Yet another alternative could be to use a very bright visible light.

Alternative Audible Reliable Readiness Indicators

Remaining with FIG. 8, if the defibrillator otherwise has power (e.g., the lack of readiness may be due to a failure of a self-test), the lack of readiness could be indicated by a very loud warning tone. In this embodiment, the WCD 800 is configured with an audible output device 830, such as a speaker. If tones (or voice prompts) are used to indicate unreadiness, then the warning tone should not start until the patient has had a reasonable amount of time to apply the device. For example, as the patient is getting dressed in the morning they may need to put a new battery in the device, put the garment on, and connect the garment 801 to the defibrillator 821. The readiness indicator 830 should allow a sufficient amount of time to complete these steps before warning the patient that something was done incorrectly.

One approach would be for a tone to start at a relatively low volume as soon as the battery is inserted, then to progressively increase in volume (or frequency or other measure of intensity) until the garment 801 is completely ready for use. Alternatively, voice prompts could be given that get progressively more insistent, starting with instructions, like "connect electrodes," and changing to more dire warnings if the device is not correctly applied, like "You are NOT protected! Connect electrodes NOW! The garment is NOT ready for use!"

Fail Safe Readiness Indicators

Figure 9:
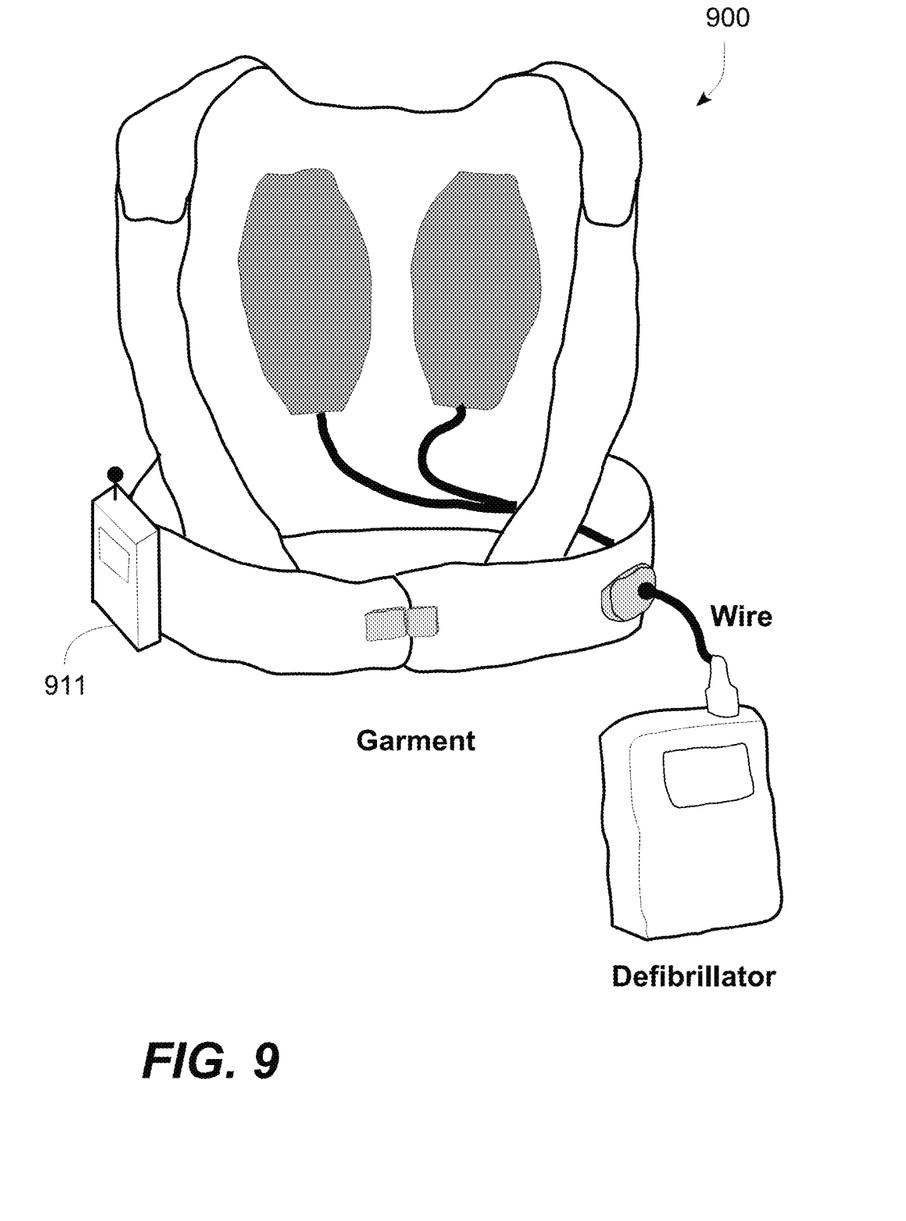
FIG. 9 illustrates still another embodiment of a reliable readiness indicator.

FIG. 9 illustrates still another embodiment of a reliable readiness indicator. In this embodiment, the WCD 900 includes a wireless transmission device 911, such as a wireless or cellular telephone or other means of remote communication. It is axiomatic that unreadiness warnings that require power will not work without power. Accordingly, if the defibrillator battery is discharged or disconnected, and a warning device is powered by the defibrillator battery, then the warning device will not work. They also may not work if the device has an electrical failure. For these reasons, fail-safe warning mechanisms are desirable.

As illustrated in FIG. 9, one embodiment of a fail-safe technique for providing an unreadiness indication is for the WCD 900 to periodically contact a base station (not shown) using the wireless transmission device 911. The wireless transmission device 911 may be a cellular communication device (e.g, a specially adapted cellular phone), or it may be a special purpose computing device configured with wireless communication technology. The base station may be configured to provide an unreadiness indication if it does not receive contact from the WCD 900 within the expected time frame. In this embodiment, the base station could be a unit within the home of the patient that communicates with the defibrillator with the wireless transmission device 911 using an access point of a local area network (e.g., using Wi-Fi or Bluetooth). Alternatively, the base station could also be a remote monitoring service that the WCD 900 contacts via Wi-Fi or a cellular provider. Once it is established that the device is not ready notification could be provided to the patient or to caregivers via methods described above.

In still another alternative, the WCD 900 could be configured to inform a support individual, such as a caregiver, when the device is not ready. In one example, the WCD 900 could transmit an SMS "text" message or automated phone call message using the wireless transmission device 911 if the WCD 900 is not ready for use. In one implementation, the wireless transmission device 911 could be pre-programmed with a phone number for the support individual, such as a family member, a caregiver, or a health-care provider or service. Upon receiving the transmitted notice, that support individual could then assist the patient in applying the device. If the support individual is unavailable, the device could also attempt to place a call or send a message directly to the patient to assist with the device.

It will be apparent to those skilled in the art that these techniques for indicating readiness to the patient could be done in conjunction with existing techniques, like voice prompts, indicators, or text messages. Such prompts may even be used to inform the patient about how to make the device ready for use.

Embodiments for Monitoring Electrode Shear Forces

One (of many) reasons that a wearable defibrillator device could enter a dangerous condition is because signals from ECG electrodes are complicated by noise artifacts resulting from motion of the ECG electrode relative to the skin surface on which it is adhered. Especially in ambulatory ECG monitors (Holter monitors) or wearable cardioverter defibrillators, ECG electrodes sliding across the skin surface can create non-trivial signal analysis problems. One technique to address this problem is implemented as a hybrid electrode that monitors shear forces between the ECG electrode and the skin surface using piezoelectric film sensors integrated into the ECG sensor assembly. By characterizing these shear forces, a system would be able to infer several things. For example, the fact that the ECG electrode is moving relative to the skin provides a "quality factor" for using this signal relative to others which might be more stable. The direction, velocity and acceleration of electrode movement relative to the skin could provide information about the design of the electrode retention mechanism or garment and the optimal positioning of the ECG sensors (e.g., if a given electrode is constantly sliding in a certain direction, improved designs or electrode locations could be obtained). This ability could provide information about patient activity and compliance (if the patient is constantly adjusting or moving the electrode retention mechanism or garment), as well as impact stresses experienced by the patient due to falling, bumping into something, or being hit by something.

The information obtained from the hybrid sensor could be complimentary to other signals used to infer motion artifacts, such as impedance measurements or signals from other sensors such as accelerometers.

In one embodiment, a hybrid electrode for measuring ECG and relative shear includes a "standard" ECG electrode (which might be Ag—AgCl, conductive polymer, silver fabric, etc) surrounded by one or more sensors made from a thin piezoelectric film or ceramic. The piezoelectric film would produce a signal relative to the shear forces encountered as the electrode slides across a surface (such as the patient's skin).

With a single piezoelectric sensor (e.g., a piezoelectric film in the shape of a ring surrounding and isolated from the ECG sensor), the hybrid electrode can provide information about the global shear forces seen by the assembly. One could infer if the assembly is moving, or not. This first embodiment is shown in FIG. 10, which illustrates a hybrid electrode with single piezo film sensor surrounding a central ECG sensor.

In another embodiment, multiple sensors could be placed around the ECG sensor in order to infer relative displacement, velocity and acceleration if the ECG electrode starts to slide. One example of this embodiment is shown in FIG. 11, which illustrates a hybrid electrode with multiple piezo film sensors connected to a central ECG sensor.

In this second embodiment, the piezoelectric film sensors are attached to a central hub that contains the ECG sensor via non-rigid tensile connections (e.g., a string). These tensile connections "buckle" if the ECG moves towards that piezo film, providing a delay in the response of that sensor. The opposite sensor will be immediately pulled with the ECG sensor, providing no delay. The other sensors will have delays in between. With knowledge of the geometry of the assembly and delays between the signals, a system could calculate the relative displacement and direction, velocity and acceleration of the hybrid electrode assembly. FIG. 12 illustrates one possible technique to infer direction, velocity, and acceleration of an ECG sensor based on signal delays from 4 piezo sensors.

Figure 10:
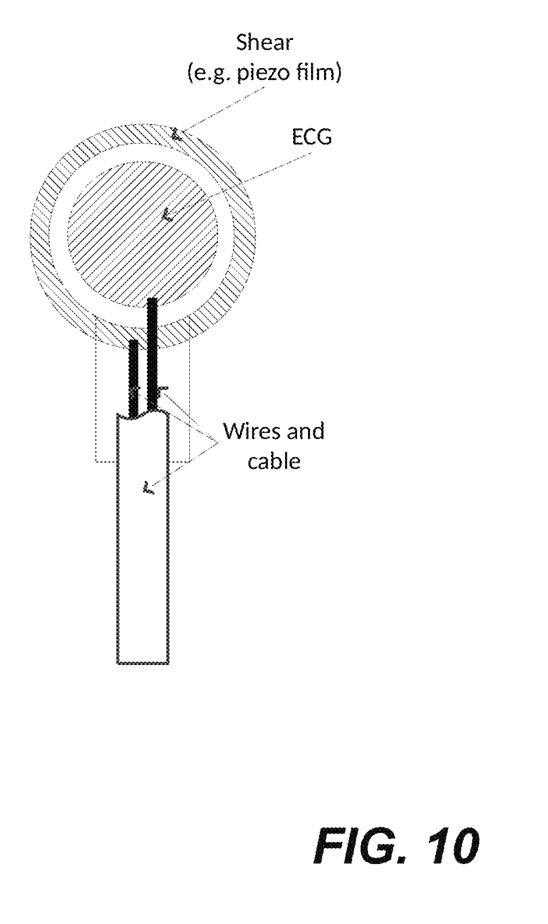
FIG. 10 illustrates a hybrid electrode with single piezo film sensor surrounding a central ECG sensor.
Figure 11:
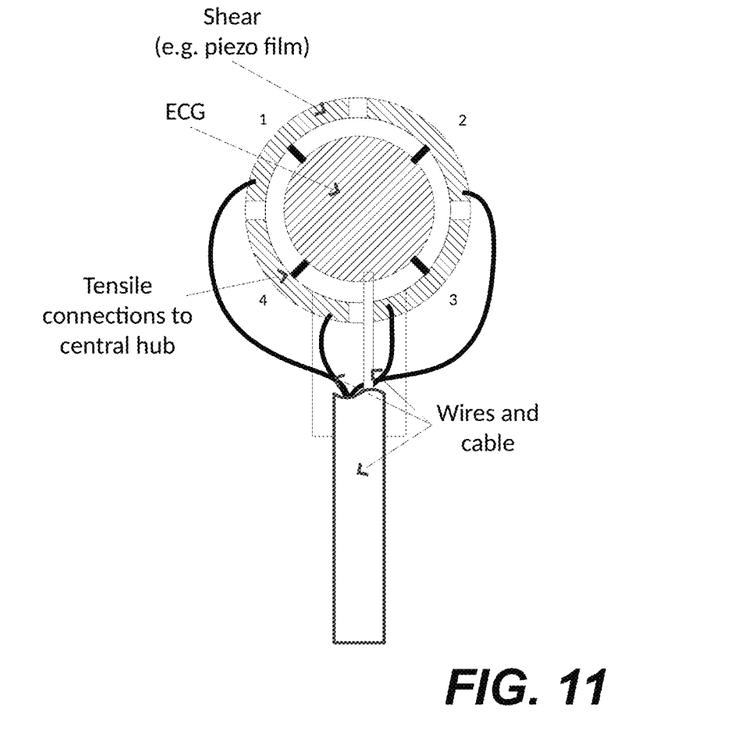
FIG. 11 illustrates a hybrid electrode with multiple piezo film sensors connected to a central ECG sensor.
Figure 12:
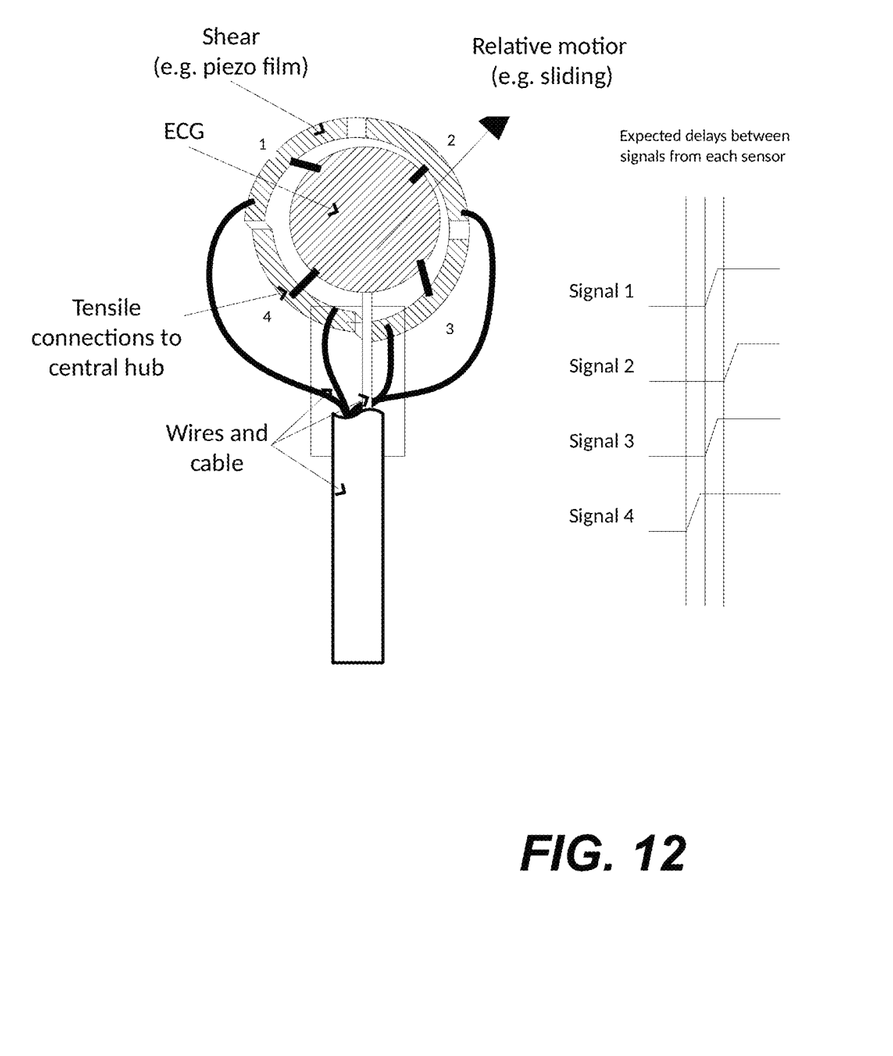
FIG. 12 illustrates one possible technique to infer direction, velocity, and acceleration of an ECG sensor based on signal delays from 4 piezo sensors.

Other embodiments may include combinations and sub-combinations of features described or shown in FIGS. 10-12, including for example, embodiments that are equivalent to providing or applying a feature in a different order than in a described embodiment, extracting an individual feature from one embodiment and inserting such feature into another embodiment; removing one or more features from an embodiment; or both removing one or more features from an embodiment and adding one or more features extracted from one or more other embodiments, while providing the advantages of the features incorporated in such combinations and sub-combinations. As used in this paragraph, "feature" or "features" can refer to structures and/or functions of an apparatus, article of manufacture or system, and/or the steps, acts, or modalities of a method.

In the foregoing description, numerous details have been set forth in order to provide a sufficient understanding of the described embodiments. In other instances, well-known features have been omitted or simplified to not unnecessarily obscure the description.

A person skilled in the art in view of this description will be able to practice the disclosed invention. The specific embodiments disclosed and illustrated herein are not to be considered in a limiting sense. Indeed, it should be readily apparent to those skilled in the art that what is described herein may be modified in numerous ways. Such ways can include equivalents to what is described herein. In addition, the invention may be practiced in combination with other systems. The following claims define certain combinations and subcombinations of elements, features, steps, and/or functions, which are regarded as novel and non-obvious. Additional claims for other combinations and subcombinations may be presented in this or a related document.

What is claimed is:

1. An apparatus, comprising:
a wearable medical device configured to treat a patient, the wearable medical device having a garment configured to be worn by the patient, the wearable medical device having a functionality that can transition between an operative state and an inoperative state; a monitor to determine when the functionality is in the inoperative state; the garment having a clasp operative to secure the garment on the patient when the functionality is in the operative state, the garment further having a solenoid in operative cooperation with the clasp, the solenoid operative to prevent the clasp from thus securing the garment when the monitored functionality is in the inoperative state.

2. The apparatus recited in claim 1, wherein the wearable medical device comprises a defibrillator, the functionality being an ability of the defibrillator to operate.

3. The apparatus recited in claim 2, wherein the defibrillator includes a battery and is configured to be powered by the battery, and wherein the functionality is in the operative state if the battery is sufficiently charged for safe operation of the defibrillator.

4. The apparatus recited in claim 2, wherein the defibrillator is configured to perform a self-test to also determine if the functionality is in the operative state.

5. The apparatus recited in claim 1, wherein the solenoid is controlled by a signal from the monitor, the signal being present only when the functionality is in the operative state.

6. The apparatus recited in claim 1, wherein the wearable medical device comprises a wearable cardioverter defibrillator.

7. A wearable medical device for treating a patient, comprising:
a medical device configured to deliver a treatment shock to the patient, the medical device having a functionality that can transition between an operative state and an inoperative state;
a monitor to determine when the functionality is in the inoperative state;
a garment configured to be worn by the patient, the garment including a clasp configured for clasping by the patient when the functionality is in the operative state; and
an active component in operative cooperation with the clasp, the active component configured to move so as to physically interfere with the patient thus clasping when the monitored functionality is in the inoperative state.

8. The wearable medical device of claim 7, in which the clasping causes the garment to be secured on the patient.

9. The wearable medical device of claim 7, in which the active component includes a solenoid with a cylinder and a plunger, and
the plunger is configured to thus move with respect to the cylinder.

10. The wearable medical device of claim 7, in which the monitor is configured to generate a signal when the functionality is in the operative state, and
the active component is controlled by the signal from the monitor.

11. The wearable medical device of claim 7, in which the medical device includes a wearable cardioverter defibrillator.

12. The wearable medical device of claim 11, in which the active component includes a solenoid with a cylinder and a plunger, and
the plunger is configured to thus move with respect to the cylinder.

13. The wearable medical device of claim 7, in which the medical device has a defibrillator, and
the functionality is an ability of the defibrillator to deliver the treatment shock.

14. The wearable medical device of claim 13, in which the active component includes a solenoid with a cylinder and a plunger, and
the plunger is configured to thus move with respect to the cylinder.

15. The wearable medical device of claim 13, in which the defibrillator includes a battery, and
the defibrillator is configured to be powered by the battery, and
the functionality is in the operative state if the battery is sufficiently charged for the defibrillator to deliver the treatment shock to the patient.

16. The wearable medical device of claim 13, in which the defibrillator is configured to perform a self-test to also determine if the functionality is in the operative state.

* * * * *